(12) United States Patent
Peterson et al.

(10) Patent No.: US 10,493,244 B2
(45) Date of Patent: Dec. 3, 2019

(54) EXTENSION TUBING STRAIN RELIEF

(71) Applicant: Becton, Dickinson and Company, Franklin Lakes, NJ (US)

(72) Inventors: Bart D. Peterson, Farmington, UT (US); Jonathan Karl Burkholz, Salt Lake City, UT (US); Bryan Fred Bihlmaier, Provo, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 328 days.

(21) Appl. No.: 15/286,212

(22) Filed: Oct. 5, 2016

(65) Prior Publication Data
US 2017/0120013 A1 May 4, 2017

Related U.S. Application Data

(60) Provisional application No. 62/296,385, filed on Feb. 17, 2016, provisional application No. 62/296,383, (Continued)

(51) Int. Cl.
*A61M 25/06* (2006.01)
*A61M 25/00* (2006.01)
(Continued)

(52) U.S. Cl.
CPC .... *A61M 25/0606* (2013.01); *A61M 25/0097* (2013.01); *F16L 35/00* (2013.01);
(Continued)

(58) Field of Classification Search
CPC . A61M 25/0606; A61M 25/0097; F16L 35/00
(Continued)

(56) References Cited

U.S. PATENT DOCUMENTS

| 1,844,023 A | 2/1932 | Terry |
| 3,223,629 A | 12/1965 | Loeffler |

(Continued)

FOREIGN PATENT DOCUMENTS

| CA | 1 331 333 C | 8/1994 |
| CA | 2133053 A1 | 3/1995 |

(Continued)

OTHER PUBLICATIONS

Anusavice KJ, Zhang N-Z, Shen C. Controlled Release of Chlorhexidine from UDMA-TEGDMA Resin, Journal of dental research, 2006;85(10); 950-954.

(Continued)

*Primary Examiner* — Phillip A Gray
(74) *Attorney, Agent, or Firm* — Kirton & McConkie; Craig Metcalf; Kevin Stinger

(57) ABSTRACT

An integrated vascular access device can include strain relief features to minimize the likelihood of the extension tubing becoming kinked during use. These strain relief features can be configured at both ends of the extension tubing to minimize the likelihood of kinking at the interfaces to the catheter adapter and luer adapter. To provide strain relief at the catheter adapter end of the extension tubing, an interface formed of a flexible material can be aligned with an extension of the catheter adapter into which the extension tubing inserts. The interface can be integrated into a stabilization platform or formed separately from a stabilization platform. To provide strain relief at the luer adapter end of the extension tubing, a flexible spacer can be coupled to a distal end of the adapter and have a distal portion that is positioned around the extension tube.

20 Claims, 4 Drawing Sheets

Related U.S. Application Data filed on Feb. 17, 2016, provisional application No. 62/247,624, filed on Oct. 28, 2015, provisional application No. 62/247,617, filed on Oct. 28, 2015, provisional application No. 62/247,599, filed on Oct. 28, 2015, provisional application No. 62/247,621, filed on Oct. 28, 2015, provisional application No. 62/247,607, filed on Oct. 28, 2015, provisional application No. 62/247,626, filed on Oct. 28, 2015, provisional application No. 62/247,596, filed on Oct. 28, 2015.

(51) Int. Cl.
  *F16L 35/00* (2006.01)
  *A61M 39/12* (2006.01)
  *A61M 25/01* (2006.01)

(52) U.S. Cl.
  CPC ......... *A61M 25/01* (2013.01); *A61M 25/0637* (2013.01); *A61M 25/0693* (2013.01); *A61M 39/12* (2013.01); *A61M 2025/0098* (2013.01)

(58) Field of Classification Search
  USPC ........................................................ 604/523
  See application file for complete search history.

(56) References Cited

U.S. PATENT DOCUMENTS

| | | |
|---|---|---|
| 3,695,921 A | 10/1972 | Shepherd et al. |
| 3,867,937 A | 2/1975 | Schwartz |
| 3,986,508 A | 10/1976 | Barrington |
| 4,068,660 A | 1/1978 | Beck |
| 4,170,996 A | 10/1979 | Wu |
| 4,280,500 A | 7/1981 | Ono |
| 4,334,551 A | 6/1982 | Pfister |
| 4,339,336 A | 7/1982 | Hammond et al. |
| 4,387,879 A | 6/1983 | Tauschinski |
| 4,449,693 A | 5/1984 | Gereg |
| 4,512,766 A | 4/1985 | Vailancourt |
| 4,584,192 A | 4/1986 | Dell et al. |
| 4,585,435 A * | 4/1986 | Vaillancourt ....... A61M 5/1408 604/126 |
| 4,592,920 A | 6/1986 | Murtfeldt |
| 4,603,152 A | 7/1986 | Laurin et al. |
| 4,610,674 A | 9/1986 | Suzuki et al. |
| 4,629,743 A | 12/1986 | Hong |
| 4,629,746 A | 12/1986 | Michl et al. |
| 4,642,126 A | 2/1987 | Zador et al. |
| 4,676,782 A | 6/1987 | Yamamoto et al. |
| 4,677,143 A | 6/1987 | Laurin et al. |
| 4,716,032 A | 12/1987 | Westfall et al. |
| 4,723,948 A | 2/1988 | Clark et al. |
| 4,758,225 A | 7/1988 | Cox et al. |
| 4,781,703 A | 11/1988 | Walker et al. |
| 4,798,594 A | 1/1989 | Hillstead |
| 4,805,933 A | 2/1989 | Swisher |
| 4,838,873 A | 6/1989 | Landskron et al. |
| 4,842,591 A | 6/1989 | Luther |
| 4,846,812 A | 7/1989 | Walker et al. |
| 4,874,377 A | 10/1989 | Newgard et al. |
| 4,880,414 A | 11/1989 | Whipple |
| 4,895,566 A | 1/1990 | Lee |
| 4,897,427 A | 1/1990 | Barnavon et al. |
| 4,915,934 A | 4/1990 | Tomlinson |
| 4,917,668 A | 4/1990 | Haindl |
| 4,925,668 A | 5/1990 | Khan et al. |
| 4,933,178 A | 6/1990 | Capelli |
| 4,935,010 A | 6/1990 | Cox et al. |
| 4,950,257 A | 8/1990 | Hibbs et al. |
| 4,955,890 A | 9/1990 | Yamamoto |
| 4,976,697 A | 12/1990 | Walder et al. |
| 4,985,399 A | 1/1991 | Matsuda et al. |
| 4,990,357 A | 2/1991 | Karakelle et al. |
| 5,019,096 A | 5/1991 | Fox, Jr. et al. |
| 5,023,082 A | 6/1991 | Friedman et al. |
| 5,030,665 A | 7/1991 | Lee et al. |
| 5,041,097 A | 8/1991 | Johnson |
| 5,053,014 A | 10/1991 | Van Heugten |
| 5,062,836 A | 11/1991 | Wendell |
| 5,064,416 A | 11/1991 | Newgard et al. |
| 5,077,352 A | 12/1991 | Elton |
| 5,078,703 A | 1/1992 | Bryant |
| 5,084,023 A | 1/1992 | Lemieux |
| 5,085,645 A | 2/1992 | Purdy et al. |
| 5,098,410 A | 3/1992 | Kerby et al. |
| 5,108,374 A | 4/1992 | Lemieux |
| 5,127,905 A | 7/1992 | Lemieux |
| 5,129,887 A * | 7/1992 | Euteneuer ........... A61M 25/104 604/533 |
| 5,154,703 A | 10/1992 | Bonaldo |
| 5,156,596 A | 10/1992 | Balbierz et al. |
| 5,167,647 A | 12/1992 | Wijkamp et al. |
| 5,217,493 A | 6/1993 | Raad et al. |
| 5,226,898 A | 7/1993 | Gross |
| 5,234,410 A | 8/1993 | Graham et al. |
| 5,242,425 A | 9/1993 | White et al. |
| 5,256,145 A | 10/1993 | Atkinson et al. |
| 5,290,246 A | 3/1994 | Yamamoto et al. |
| 5,295,969 A | 3/1994 | Fischell et al. |
| 5,330,435 A | 7/1994 | Vaillancourt |
| 5,330,449 A | 7/1994 | Prichard et al. |
| 5,350,363 A | 9/1994 | Goode et al. |
| 5,352,205 A | 10/1994 | Dales et al. |
| 5,357,636 A | 10/1994 | Dresdner, Jr. et al. |
| 5,366,505 A | 11/1994 | Farber |
| 5,380,301 A | 1/1995 | Prichard et al. |
| 5,405,323 A | 4/1995 | Rogers et al. |
| 5,405,338 A | 4/1995 | Kranys |
| 5,456,675 A | 10/1995 | Wolbring et al. |
| 5,456,948 A | 10/1995 | Mathisen et al. |
| 5,487,728 A | 1/1996 | Vaillancourt |
| 5,512,199 A | 4/1996 | Khan et al. |
| 5,520,666 A | 5/1996 | Choudhury et al. |
| 5,536,258 A | 7/1996 | Folden |
| 5,540,661 A | 7/1996 | Tomisaka et al. |
| 5,547,662 A | 8/1996 | Khan et al. |
| 5,549,566 A | 8/1996 | Elias |
| 5,549,577 A | 8/1996 | Siegel et al. |
| 5,575,769 A | 11/1996 | Vaillancourt |
| 5,589,120 A | 12/1996 | Khan et al. |
| 5,613,663 A | 3/1997 | Schmidt et al. |
| 5,616,338 A | 4/1997 | Fox, Jr. et al. |
| 5,620,434 A | 4/1997 | Brony |
| 5,629,006 A | 5/1997 | Hoang et al. |
| 5,638,812 A | 6/1997 | Turner |
| 5,651,772 A | 7/1997 | Arnett |
| 5,653,695 A | 8/1997 | Hopkins et al. |
| 5,657,963 A | 8/1997 | Hinchliffe et al. |
| 5,658,253 A | 8/1997 | Piontek et al. |
| 5,676,656 A | 10/1997 | Brimhall |
| 5,688,747 A | 11/1997 | Khan et al. |
| 5,697,915 A | 12/1997 | Lynn |
| 5,698,229 A | 12/1997 | Ohsumi et al. |
| 5,712,229 A | 1/1998 | Hopkins et al. |
| 5,716,406 A | 2/1998 | Farber |
| 5,718,678 A * | 2/1998 | Fleming, III ..... A61M 25/0009 604/43 |
| 5,738,144 A | 4/1998 | Rogers |
| 5,749,861 A | 5/1998 | Guala et al. |
| 5,763,412 A | 6/1998 | Khan et al. |
| 5,773,487 A | 6/1998 | Sokol |
| 5,806,831 A | 9/1998 | Paradis |
| 5,810,768 A | 9/1998 | Lopez |
| 5,817,069 A | 10/1998 | Arnett |
| 5,827,239 A | 10/1998 | Dillon et al. |
| 5,830,196 A | 11/1998 | Hicks |
| 5,830,401 A | 11/1998 | Prichard et al. |
| 5,833,674 A | 11/1998 | Turnbull et al. |
| 5,843,046 A | 12/1998 | Motisi et al. |
| 5,861,440 A | 1/1999 | Gohla et al. |
| 5,911,710 A | 6/1999 | Barry et al. |
| 5,951,519 A | 9/1999 | Utterberg |

(56) References Cited

U.S. PATENT DOCUMENTS

| | | |
|---|---|---|
| 5,954,698 A | 9/1999 | Pike |
| 5,957,898 A | 9/1999 | Jepson |
| 5,967,490 A | 10/1999 | Pike |
| 6,039,302 A | 3/2000 | Cote, Sr. et al. |
| 6,046,143 A | 4/2000 | Khan et al. |
| 6,051,609 A | 4/2000 | Yu et al. |
| 6,068,622 A | 5/2000 | Sater et al. |
| 6,074,379 A | 6/2000 | Prichard |
| 6,077,244 A | 6/2000 | Botich et al. |
| 6,102,890 A | 8/2000 | Stivland et al. |
| 6,117,108 A | 9/2000 | Woehr et al. |
| 6,120,784 A | 9/2000 | Snyder, Jr. |
| 6,127,320 A | 10/2000 | van Ooij et al. |
| 6,156,054 A | 12/2000 | Zadno-Azizi et al. |
| 6,165,168 A | 12/2000 | Russo |
| 6,171,287 B1 | 1/2001 | Lynn et al. |
| 6,217,566 B1 | 4/2001 | Ju et al. |
| 6,228,073 B1 | 5/2001 | Noone et al. |
| 6,242,526 B1 | 6/2001 | Siddiqui et al. |
| 6,245,098 B1 | 6/2001 | Feeser et al. |
| 6,248,811 B1 | 6/2001 | Ottersbach et al. |
| 6,273,404 B1 | 8/2001 | Holman et al. |
| 6,273,869 B1 | 8/2001 | Vaillancourt |
| 6,322,847 B1 | 11/2001 | Zhong et al. |
| 6,326,417 B1 | 12/2001 | Jia |
| 6,332,874 B1 | 12/2001 | Eliasen et al. |
| 6,337,357 B1 | 1/2002 | Fukunishi et al. |
| 6,344,218 B1 | 2/2002 | Dodd et al. |
| 6,353,041 B1 | 3/2002 | Qian |
| 6,387,075 B1 | 5/2002 | Stivland et al. |
| 6,413,539 B1 | 7/2002 | Shalaby |
| 6,426,373 B1 | 7/2002 | Stange |
| 6,475,434 B1 | 11/2002 | Darouiche |
| 6,485,473 B1 | 11/2002 | Lynn |
| 6,488,942 B1 | 12/2002 | Ingemann |
| 6,492,445 B2 | 12/2002 | Siddiqui et al. |
| 6,503,353 B1 | 1/2003 | Peterson et al. |
| 6,511,462 B1 | 1/2003 | Itou et al. |
| 6,544,214 B1 | 4/2003 | Utterberg |
| 6,575,958 B1 | 6/2003 | Happ et al. |
| 6,575,960 B2 | 6/2003 | Becker et al. |
| 6,576,633 B1 | 6/2003 | Young et al. |
| 6,579,221 B1 | 6/2003 | Peterson |
| 6,579,539 B2 | 6/2003 | Lawson et al. |
| 6,595,981 B2 | 7/2003 | Huet |
| 6,663,614 B1 | 12/2003 | Carter |
| 6,699,221 B2 | 3/2004 | Vaillancourt |
| 6,719,726 B2 | 4/2004 | Meng et al. |
| 6,719,991 B2 | 4/2004 | Darouiche et al. |
| 6,723,350 B2 | 4/2004 | Burrell et al. |
| 6,740,063 B2 | 5/2004 | Lynn |
| 6,808,161 B1 | 10/2004 | Hishikawa |
| 6,824,553 B1 | 11/2004 | Samson et al. |
| 6,843,784 B2 | 1/2005 | Modak et al. |
| 6,846,846 B2 | 1/2005 | Modak et al. |
| 6,861,060 B1 | 3/2005 | Luriya et al. |
| 6,883,778 B1 | 4/2005 | Newton et al. |
| 6,887,270 B2 | 5/2005 | Miller et al. |
| 6,893,456 B2 | 5/2005 | Lumauig |
| 6,896,889 B2 | 5/2005 | Chevalier et al. |
| 7,008,404 B2 | 3/2006 | Nakajima |
| 7,074,839 B2 | 7/2006 | Fansler et al. |
| 7,098,256 B2 | 8/2006 | Ong et al. |
| 7,115,183 B2 | 10/2006 | Larson et al. |
| 7,179,849 B2 | 2/2007 | Terry |
| 7,198,800 B1 | 4/2007 | Ko |
| 7,232,428 B1 | 6/2007 | Inukai et al. |
| 7,232,540 B2 | 6/2007 | Gould et al. |
| 7,261,925 B2 | 8/2007 | Nesbitt |
| 7,268,165 B2 | 9/2007 | Greten et al. |
| 7,347,839 B2 | 3/2008 | Hiejima |
| 7,374,798 B2 | 5/2008 | Choo |
| 7,396,346 B2 | 7/2008 | Nakajima |
| 7,407,707 B2 | 8/2008 | Gould et al. |
| 7,462,401 B2 | 12/2008 | Halfyard et al. |
| 7,470,254 B2 | 12/2008 | Basta et al. |
| 7,494,339 B2 | 2/2009 | Dias et al. |
| 7,498,367 B2 | 3/2009 | Qian |
| 7,514,477 B2 | 4/2009 | Klare et al. |
| 7,608,082 B2 | 10/2009 | Cuevas et al. |
| 7,704,935 B1 | 4/2010 | Davis et al. |
| 7,736,339 B2 | 6/2010 | Woehr et al. |
| 7,816,434 B2 | 10/2010 | Hackbarth et al. |
| 7,871,649 B2 | 1/2011 | Modak et al. |
| 7,874,467 B2 | 1/2011 | Pardes et al. |
| 7,914,494 B2 | 3/2011 | Hiejima |
| 8,034,454 B2 | 10/2011 | Terry |
| 8,034,455 B2 | 10/2011 | Wang |
| 8,067,402 B2 | 11/2011 | Whiteford et al. |
| 8,133,423 B2 | 3/2012 | Tang |
| 8,227,050 B1 | 7/2012 | O'Neil |
| 8,231,602 B2 | 7/2012 | Anderson et al. |
| 8,263,102 B2 | 9/2012 | Labrecque et al. |
| 8,268,381 B2 | 9/2012 | Whiteford et al. |
| 8,343,523 B2 | 1/2013 | Toreki et al. |
| 8,343,525 B2 | 1/2013 | Davis et al. |
| 8,353,876 B2 | 1/2013 | Suwito et al. |
| 8,357,119 B2 | 1/2013 | Stout et al. |
| 8,388,583 B2 | 3/2013 | Stout et al. |
| 8,414,547 B2 | 4/2013 | DiFiore et al. |
| 8,512,294 B2 | 8/2013 | Ou-Yang et al. |
| 8,622,995 B2 | 1/2014 | Ziebol |
| 8,622,996 B2 | 1/2014 | Ziebol |
| 8,691,887 B2 | 4/2014 | Ou-Yang |
| 8,728,030 B2 | 5/2014 | Woehr |
| 8,840,927 B2 | 9/2014 | DiTizio et al. |
| 9,078,441 B2 | 7/2015 | Raad |
| 9,138,252 B2 | 9/2015 | Bierman et al. |
| 2001/0010016 A1 | 7/2001 | Modak et al. |
| 2001/0016589 A1 | 8/2001 | Modak et al. |
| 2001/0018095 A1 | 8/2001 | Shlenker et al. |
| 2001/0032006 A1 | 10/2001 | Griffin |
| 2001/0049519 A1 | 12/2001 | Holman et al. |
| 2001/0053895 A1 | 12/2001 | Vaillancourt |
| 2001/0056133 A1 | 12/2001 | Montgomery et al. |
| 2002/0009436 A1 | 1/2002 | Doyle et al. |
| 2002/0022660 A1 | 2/2002 | Jampani et al. |
| 2002/0028751 A1 | 3/2002 | Lokkesmoe et al. |
| 2002/0037260 A1 | 3/2002 | Budny et al. |
| 2002/0040092 A1 | 4/2002 | Siddiqui et al. |
| 2002/0064858 A1 | 5/2002 | Yacoby-Zeevi |
| 2002/0091424 A1 | 7/2002 | Biel |
| 2002/0119111 A1 | 8/2002 | Kilgour et al. |
| 2002/0133124 A1 | 9/2002 | Leinsing et al. |
| 2002/0144705 A1 | 10/2002 | Brattesani et al. |
| 2003/0023208 A1 | 1/2003 | Osypka et al. |
| 2003/0060804 A1 | 3/2003 | Vaillancourt |
| 2003/0068667 A1 | 4/2003 | Olson et al. |
| 2003/0072781 A1 | 4/2003 | Pelerin |
| 2003/0105143 A1 | 6/2003 | Ammendola et al. |
| 2003/0119932 A1 | 6/2003 | Al-Akhdar et al. |
| 2003/0134783 A1 | 7/2003 | Harshey et al. |
| 2003/0144362 A1 | 7/2003 | Utterberg et al. |
| 2003/0147932 A1 | 8/2003 | Nun et al. |
| 2003/0162839 A1 | 8/2003 | Symington et al. |
| 2003/0170308 A1 | 9/2003 | Cleary et al. |
| 2003/0176848 A1 | 9/2003 | Gibson et al. |
| 2003/0206875 A1 | 11/2003 | Budny et al. |
| 2003/0215433 A1 | 11/2003 | Kokai-Kun et al. |
| 2003/0224032 A1 | 12/2003 | Read et al. |
| 2004/0013574 A1 | 1/2004 | Conway |
| 2004/0013703 A1 | 1/2004 | Ralph et al. |
| 2004/0014864 A1 | 1/2004 | Milic et al. |
| 2004/0039349 A1 | 2/2004 | Modak et al. |
| 2004/0058829 A1 | 3/2004 | Hei et al. |
| 2004/0062592 A1 | 4/2004 | Shekalim |
| 2004/0109852 A1 | 6/2004 | Xu |
| 2004/0115477 A1 | 6/2004 | Nesbitt |
| 2004/0132164 A1 | 7/2004 | Doyle et al. |
| 2004/0180829 A1 | 9/2004 | Bassler et al. |
| 2004/0185296 A1 | 9/2004 | Mazzanti |
| 2004/0230162 A1 | 11/2004 | Tan |
| 2004/0234475 A1 | 11/2004 | Lannibois-Drean et al. |
| 2005/0008671 A1 | 1/2005 | Van Antwerp |

(56) References Cited

U.S. PATENT DOCUMENTS

| | | |
|---|---|---|
| 2005/0048005 A1 | 3/2005 | Stockel |
| 2005/0048124 A1 | 3/2005 | Sarangapani |
| 2005/0059731 A1 | 3/2005 | Albrecht et al. |
| 2005/0080158 A1 | 4/2005 | Ong et al. |
| 2005/0100580 A1 | 5/2005 | Osborne et al. |
| 2005/0118239 A1 | 6/2005 | Sabesan |
| 2005/0124970 A1 | 6/2005 | Kunin et al. |
| 2005/0131356 A1 | 6/2005 | Ash et al. |
| 2005/0143286 A1 | 6/2005 | Singh et al. |
| 2005/0147525 A1 | 7/2005 | Bousquet |
| 2005/0148928 A1 | 7/2005 | Molina et al. |
| 2005/0158253 A1 | 7/2005 | Budny et al. |
| 2005/0176905 A1 | 8/2005 | Moon et al. |
| 2005/0209581 A1 | 9/2005 | Butts et al. |
| 2005/0209583 A1 | 9/2005 | Powers et al. |
| 2005/0233950 A1 | 10/2005 | Madhyastha |
| 2005/0265931 A1 | 12/2005 | Qian |
| 2006/0024372 A1 | 2/2006 | Utterberg et al. |
| 2006/0051385 A1 | 3/2006 | Scholz |
| 2006/0064159 A1 | 3/2006 | Porter et al. |
| 2006/0163515 A1 | 7/2006 | Ruschke |
| 2006/0165751 A1 | 7/2006 | Chudzik et al. |
| 2006/0165903 A1 | 7/2006 | Mazzanti |
| 2006/0177477 A1 | 8/2006 | Ash et al. |
| 2006/0239954 A1 | 10/2006 | Sancho |
| 2006/0258780 A1 | 11/2006 | Chaussade et al. |
| 2006/0259012 A1 | 11/2006 | Propp et al. |
| 2006/0281663 A1 | 12/2006 | Asmus |
| 2007/0000407 A1 | 1/2007 | Leong |
| 2007/0083157 A1 | 4/2007 | Belley et al. |
| 2007/0083162 A1 | 4/2007 | O'Reagan et al. |
| 2007/0093762 A1 | 4/2007 | Utterberg et al. |
| 2007/0112112 A1 | 5/2007 | Kerschner et al. |
| 2007/0112146 A1 | 5/2007 | Falk et al. |
| 2007/0129690 A1 | 6/2007 | Rosenblatt et al. |
| 2007/0141524 A1 | 6/2007 | Brennan et al. |
| 2007/0160547 A1 | 7/2007 | Duffy et al. |
| 2007/0166344 A1 | 7/2007 | Qu et al. |
| 2007/0202177 A1 | 8/2007 | Hoang |
| 2007/0203574 A1 | 8/2007 | McGrath et al. |
| 2007/0225179 A1 | 9/2007 | Schutz et al. |
| 2007/0233007 A1 | 10/2007 | Adams |
| 2007/0275101 A1 | 11/2007 | Lu et al. |
| 2007/0281198 A1 | 12/2007 | Lousenberg |
| 2008/0026026 A1 | 1/2008 | Lu et al. |
| 2008/0027410 A1 | 1/2008 | Harding |
| 2008/0033371 A1 | 2/2008 | Updegraff et al. |
| 2008/0039796 A1 | 2/2008 | Nakajima |
| 2008/0051737 A1 | 2/2008 | Paul et al. |
| 2008/0075761 A1 | 3/2008 | Modak et al. |
| 2008/0103487 A1 | 5/2008 | Miyasaka |
| 2008/0108944 A1 | 5/2008 | Woehr et al. |
| 2008/0119789 A1 | 5/2008 | Kaemmerer |
| 2008/0161763 A1 | 7/2008 | Harding et al. |
| 2008/0182921 A1 | 7/2008 | Suh et al. |
| 2008/0194707 A1 | 8/2008 | Potter |
| 2008/0319387 A1 | 12/2008 | Amisar et al. |
| 2009/0012220 A1 | 1/2009 | Yamane et al. |
| 2009/0036768 A1 | 2/2009 | Seehusen |
| 2009/0062766 A1 | 3/2009 | Howlett |
| 2009/0101152 A1 | 4/2009 | Burk et al. |
| 2009/0110844 A1 | 4/2009 | Platzer et al. |
| 2009/0114327 A1 | 5/2009 | Breunig |
| 2009/0117164 A1 | 5/2009 | Toreki et al. |
| 2009/0125118 A1 | 5/2009 | Gong |
| 2009/0157007 A1 | 6/2009 | McKinnon |
| 2009/0162530 A1 | 6/2009 | Nesbitt |
| 2009/0176907 A1 | 7/2009 | Subramanian et al. |
| 2009/0188559 A1 | 7/2009 | Nesbitt |
| 2009/0220739 A1 | 9/2009 | Chougule |
| 2009/0226541 A1 | 9/2009 | Scholz et al. |
| 2009/0281525 A1 | 11/2009 | Harding et al. |
| 2009/0317435 A1 | 12/2009 | Vandesteeg et al. |
| 2009/0324666 A1 | 12/2009 | Krongauz et al. |
| 2009/0324738 A1 | 12/2009 | Krongauz |
| 2010/0015200 A1 | 1/2010 | McClain |
| 2010/0024648 A1 | 2/2010 | Breault |
| 2010/0069854 A1 | 3/2010 | Okoh |
| 2010/0106102 A1 | 4/2010 | Ziebol et al. |
| 2010/0106103 A1 | 4/2010 | Ziebol |
| 2010/0135949 A1 | 6/2010 | Ou-Yang |
| 2010/0136209 A1 | 6/2010 | Ou-Yang et al. |
| 2010/0137379 A1 | 6/2010 | Ou-Yang |
| 2010/0137472 A1 | 6/2010 | Ou-Yang |
| 2010/0200017 A1 | 8/2010 | Kerr |
| 2010/0204648 A1 | 8/2010 | Stout et al. |
| 2010/0204675 A1 | 8/2010 | Woehr et al. |
| 2010/0222746 A1 | 9/2010 | Burkholz |
| 2011/0009831 A1 | 1/2011 | Burkholz et al. |
| 2011/0044850 A1 | 2/2011 | Solomon et al. |
| 2011/0065798 A1 | 3/2011 | Hoang et al. |
| 2011/0146680 A1 | 6/2011 | Conway |
| 2011/0150958 A1 | 6/2011 | Davis et al. |
| 2011/0160662 A1 | 6/2011 | Stout |
| 2011/0160663 A1 | 6/2011 | Stout et al. |
| 2011/0218529 A1 | 9/2011 | Garcia et al. |
| 2011/0301553 A1 | 12/2011 | Goral et al. |
| 2011/0319825 A1 | 12/2011 | Goral et al. |
| 2012/0016318 A1 | 1/2012 | Hoang et al. |
| 2012/0078203 A1 | 3/2012 | Gaube et al. |
| 2012/0083750 A1 | 4/2012 | Sansoucy |
| 2012/0103448 A1 | 5/2012 | Hopf et al. |
| 2012/0111368 A1 | 5/2012 | Rahimy et al. |
| 2013/0090607 A1 | 4/2013 | McKinnon |
| 2013/0165868 A1 | 6/2013 | Isaacson et al. |
| 2013/0171030 A1 | 7/2013 | Ferlic et al. |
| 2013/0196079 A1 | 8/2013 | Schwalm et al. |
| 2013/0197485 A1 | 8/2013 | Gardner et al. |
| 2013/0204231 A1 | 8/2013 | Ziebol et al. |
| 2013/0245568 A1 | 9/2013 | Kerr |
| 2013/0274686 A1 | 10/2013 | Ziebol |
| 2013/0310764 A1 | 11/2013 | Burkholz |
| 2013/0330387 A1 | 12/2013 | Ou-Yang |
| 2016/0008517 A1 | 1/2016 | Burkholz et al. |
| 2017/0095596 A1 | 4/2017 | Petrak et al. |

FOREIGN PATENT DOCUMENTS

| | | |
|---|---|---|
| CN | 1187598 A | 7/1998 |
| CN | 1526771 A | 9/2004 |
| CN | 101353545 A | 1/2009 |
| CN | 102070983 A | 5/2011 |
| CN | 102481391 | 5/2012 |
| CN | 102497894 | 6/2012 |
| DE | 821629 | 11/1951 |
| DE | 2104745 | 8/1972 |
| DE | 3314640 | 11/1983 |
| DE | 3913392 C2 | 10/1990 |
| DE | 40 11 867 A1 | 10/1991 |
| DE | 202009009602 U1 | 12/2009 |
| EP | 0 036 294 A2 | 9/1981 |
| EP | 0 070 087 A1 | 1/1983 |
| EP | 0 227 230 A1 | 7/1987 |
| EP | 0328421 | 8/1989 |
| EP | 0 338 418 A1 | 10/1989 |
| EP | 0 370 997 A2 | 5/1990 |
| EP | 0379271 B1 | 7/1990 |
| EP | 0 396 431 A1 | 11/1990 |
| EP | 0 414 997 A1 | 3/1991 |
| EP | 484092 | 5/1992 |
| EP | 0 778 337 A2 | 6/1997 |
| EP | 1 466 645 A2 | 10/2004 |
| EP | 1679043 B1 | 7/2006 |
| EP | 0 992 252 B1 | 8/2006 |
| EP | 2868722 | 5/2015 |
| JP | H05-277434 A | 10/1993 |
| JP | 07-051651 A | 2/1995 |
| JP | H0747435A B2 | 2/1995 |
| JP | 08-182764 | 7/1996 |
| JP | H08-209064 A | 8/1996 |
| JP | H08-311373 A | 11/1996 |
| JP | 09-151262 A | 6/1997 |
| JP | H09-157548 A | 6/1997 |
| JP | H09-176677 A | 7/1997 |

(56) References Cited

FOREIGN PATENT DOCUMENTS

| | | |
|---|---|---|
| JP | 09-324135 | 12/1997 |
| JP | H10-231 A | 1/1998 |
| JP | H10-192415 | 7/1998 |
| JP | H11-507275 | 6/1999 |
| JP | H11322560 B2 | 11/1999 |
| JP | 2000-178475 A | 6/2000 |
| JP | 2000-264803 A | 9/2000 |
| JP | 2001-072438 A | 3/2001 |
| JP | 2002510774 | 4/2002 |
| JP | 2002/282762 A | 10/2002 |
| JP | 2003-342402 A | 12/2003 |
| JP | 2004-043669 A | 2/2004 |
| JP | 2005-028209 A | 2/2005 |
| JP | 2005512610 | 5/2005 |
| JP | 2005-515838 A | 6/2005 |
| JP | 2005-520912 A | 7/2005 |
| JP | 2007-016096 A | 1/2007 |
| JP | 2008-533051 A | 8/2008 |
| JP | 2009-527356 | 7/2009 |
| JP | 2009-528360 | 8/2009 |
| JP | 2009-544454 | 12/2009 |
| JP | 2010-174075 | 8/2010 |
| JP | 2010536836 B2 | 12/2010 |
| JP | 2012-510559 | 5/2012 |
| JP | 2012100762 | 5/2012 |
| JP | 2012-532681 A | 12/2012 |
| JP | 2013-505062 | 2/2013 |
| JP | 2013540486 | 11/2013 |
| JP | 2015-519303 | 7/2015 |
| KR | 2002-0066429 A | 8/2002 |
| KR | 10-2008-0039460 A | 5/2008 |
| WO | 82/00413 | 2/1982 |
| WO | 94/22522 A1 | 10/1994 |
| WO | 95/21648 A1 | 8/1995 |
| WO | 96/16690 A1 | 6/1996 |
| WO | 96/40359 A1 | 12/1996 |
| WO | 98/58690 A2 | 12/1998 |
| WO | 98/58989 A1 | 12/1998 |
| WO | PCT-9858989 A1 | 12/1998 |
| WO | 99/16498 A1 | 4/1999 |
| WO | 99/32168 A1 | 7/1999 |
| WO | 99/34849 A1 | 7/1999 |
| WO | 99/36490 A1 | 7/1999 |
| WO | 99/43971 A1 | 9/1999 |
| WO | 99/44654 | 9/1999 |
| WO | 00/12171 | 3/2000 |
| WO | 00/66189 A2 | 11/2000 |
| WO | 00/74743 A1 | 12/2000 |
| WO | 01/47592 | 7/2001 |
| WO | 01/95862 A1 | 12/2001 |
| WO | 02/051464 | 7/2002 |
| WO | 2004/071568 A1 | 8/2004 |
| WO | 2004/108091 A2 | 12/2004 |
| WO | 2005/037340 A2 | 4/2005 |
| WO | 2006/012446 A2 | 2/2006 |
| WO | 2006/056482 A1 | 6/2006 |
| WO | 2006/074666 A2 | 7/2006 |
| WO | 2006/088288 A1 | 8/2006 |
| WO | 2006/099358 A2 | 9/2006 |
| WO | 2006/100442 A1 | 9/2006 |
| WO | PCT-2006-099359 A2 | 9/2006 |
| WO | 2007/052656 | 5/2007 |
| WO | 2007/064835 A2 | 6/2007 |
| WO | 2007/095576 A2 | 8/2007 |
| WO | 2007/100653 A2 | 9/2007 |
| WO | 2007/100776 A2 | 9/2007 |
| WO | 2008/014438 A2 | 1/2008 |
| WO | 2008/014447 A2 | 1/2008 |
| WO | 2008/031601 A1 | 3/2008 |
| WO | 2008/045761 A2 | 4/2008 |
| WO | PCT-2008052790 A2 | 5/2008 |
| WO | 2008/128896 A2 | 10/2008 |
| WO | 2008/132045 A2 | 11/2008 |
| WO | PCT-2009012336 A1 | 1/2009 |
| WO | 2009/055949 | 5/2009 |
| WO | 2009/070227 A1 | 6/2009 |
| WO | PCT-2009114833 A1 | 9/2009 |
| WO | 2010/034470 | 4/2010 |
| WO | PCT-2010093791 A1 | 8/2010 |
| WO | PCT-2011005951 A2 | 1/2011 |
| WO | 2011/034675 A2 | 3/2011 |
| WO | 2011/048204 A2 | 4/2011 |
| WO | 2011/118680 A1 | 9/2011 |
| WO | PCT-2012036916 A1 | 3/2012 |
| WO | 2013/009998 A2 | 1/2013 |
| WO | 2013/134421 A1 | 9/2013 |
| WO | 2014/031774 | 2/2014 |
| WO | 2015/13709 | 9/2015 |
| WO | 2015/133281 | 9/2015 |

OTHER PUBLICATIONS

McDonnell, G., et al., "Antiseptics and Disinfectants: Activity, Action, and Resistance," Clinical Microbiology Reviews, Jan. 1999, vol. 12, No. 1, pp. 149-179.

"Address Multi-Drug Resistant Organisms on the Skin with Early Preop Prep," Sage Products, Inc., Retrieved from the Internet URL: http://www.sageproducts.com/products/ssi-prevention.cfm, on Oct. 31, 2008, p. 1.

"ChloraPrep," Enturia, Retrieved from the Internet URL: http://www.enturia.com/products/chloraPrep/chloraPrep-product.html, on Oct. 31, 2008, p. 1-3.

"Ciba Irgacure 500," data sheet from Ciba Speciality Chemicals Inc., Retrieved from the Internet URL: http://www.conquimica.com/wp-content/uploads/2015/06/ft_irgacure_500.pdf, on Dec. 12, 2015, p. 1-3.

"Clinell Alcoholic 2% Chlorhexidine," Gama Healthcare, Retrieved from the Internet URL: http://www.gamahealthcare.com/clinellaca2c.html, on Nov. 7, 2008, p. 1-3.

"ComfortCoat Hydrophilic Coating," DSM in Medical, Retrieved from the internet URL: http://www.dsm.com/en_US/medical/public/home/pages/product-coating-comfortcoat.jsp, updated Jan. 11, 2013, on Apr. 22, 2013.

"Lubricent-Lubricious Hydrophillic Coatings for Medical Devices," Harland Medical Systems, Retrieved from the Internet URL: http://www.harlandmedical.com/index.php/materials/lubricent.html, on Apr. 22, 2013, p. 1-2.

"Preoperative Skin Preparation for the Surgical Patient," Sage Products, Inc., Retrieved from the internet URL: http://www.sageproducts.com/products/skin-prep.cfm, on Oct. 31, 2008, p. 1.

"Preoperative Skin Preparation and Peri operative Oral Care for the Short-Term Ventilated Patient," Sage Products, Inc., Retrieved from the internet URL: http://www.sageproducts.com/products/ssi-vap-prevention.cfm, on Oct. 31, 2008, p. 1.

"Using Silicas and Aluminas in Coatings," Retrieved from the Internet URL: www.cabot-corp.com/Silicas-And-Aluminas/Coatings, on Apr. 26, 2011.

"UV & EB Cure," Xiper Innovations, Inc., Retrieved from the internet URL: http://xiperinnovations.com/uv-eb-cure, on Mar. 16, 2017.

Silva, E., "Respecting Hydrology Science in the Patenting System," Jan. 13, 2011, pp. 1-7.

* cited by examiner

EXTENSION TUBING STRAIN RELIEF

RELATED APPLICATIONS

This application claims the benefit of U.S. Provisional Patent Application Ser. No. 62/247,624, which was filed Oct. 28, 2015, U.S. Provisional Patent Application No. 62/247,596, which was filed on Oct. 28, 2015, U.S. Provisional Patent Application No. 62/296,383, which was filed on Feb. 17, 2016, U.S. Provisional Patent Application No. 62/247,599, which was filed Oct. 28, 2015, U.S. Provisional Patent Application No. 62/247,617, which was filed on Oct. 28, 2015, U.S. Provisional Patent Application Ser. No. 62/247,607, which was filed Oct. 28, 2015, U.S. Provisional Patent Application Ser. No. 62/247,621, which was filed Oct. 28, 2015, U.S. Provisional Application No. 62/247,626, which was filed on Oct. 28, 2015, and U.S. Provisional Application No. 62/296,385, which was filed on Feb. 17, 2016, each of which is incorporated herein by reference in their entirety.

BACKGROUND

When a vascular access device is identified as being "closed" or "integrated," it generally refers to the fact that the device is configured to prevent blood from escaping the device during insertion of the catheter. Typically, such IV access devices accomplish this by integrating an extension set with the catheter adapter.

FIG. 1 illustrates an example of a prior art closed vascular access device 100. Device 100 includes a catheter adapter 101 from which a catheter 101a extends, a needle hub 102 from which a needle 102a extends, extension tubing 103 that is coupled to catheter adapter 101 at one end and includes a Y-adapter 104 coupled to the other end, and a clamp 107 for blocking or limiting fluid flow through extension tube 103. Y-adapter 104 includes a port 105 and a vent plug 106. Although a Y-adapter is shown, any type of luer adapter could be used. Device 100 can be a closed system by incorporating fluid flow blocking components (e.g., a septum or vent) into each external opening of the device such as into a proximal end of catheter adapter 101 and into any ports in adapter 104.

Catheter adapter 101 includes a stabilization platform that is comprised of a first side 101b and a second side 101c. Catheter adapter 101 also includes an extension 101d that extends from a main body portion 101e of catheter adapter 101. Access device 100 can be referred to as "integrated" because an end of extension tubing 103 inserts into and is secured within extension 101d such that extension tubing 103 is fluidly coupled to catheter 101a via a lumen of catheter adapter 101.

In access device 100, extension tubing 103 may kink at the interface between extension tubing 103 and extension 101d. Similarly, extension tubing 103 may also kink at the interface between extension tubing 103 and luer adapter 104.

BRIEF SUMMARY OF THE INVENTION

The present invention is generally directed to an integrated vascular access device that includes strain relief features to reduce the likelihood of the extension tubing becoming kinked during use. These strain relief features can be configured at both ends of the extension tubing to minimize the likelihood of kinking at the interfaces to the catheter adapter and luer adapter.

To provide strain relief at the catheter adapter end of the extension tubing, an extension of the catheter adapter into which the extension tubing inserts can be integrated into a side of a stabilization platform. Various components and/or surfaces of the present invention may comprise a soft, flexible material to assist the user in gripping the components, and/or to provide strain relief to a desired component. In some embodiments, a flexible material comprises a soft polymer having a durometer hardness of from approximately 30 Shore A to approximately 90 Shore D. In some embodiments, a flexible material comprises a soft polymer having a durometer hardness from approximately 50 Shore A to approximately 90 Shore D.

In some embodiments, the stabilization platform is formed of a flexible material. This flexible material can also be used to form an end portion of the extension. In this way, the end portion of the extension, which forms the interface between the extension tubing and the catheter adapter, is allowed to flex to minimize the likelihood that the extension tubing will become kinked. Alternatively, this interface can be formed separately from the stabilization platform including in embodiments where the catheter may or may not include a stabilization platform.

To provide strain relief at the luer adapter end of the extension tubing, a spacer comprising a flexible material can be positioned around the extension tubing and coupled to an end of the luer adapter. The flexible spacer therefore provides reinforcement at the interface between the extension tubing and the luer adapter and is allowed to flex to minimize the likelihood of kinking. In some embodiments, the flexible spacer can also be sized to block a clamp from extending overtop or contacting the rigid portion of the luer adapter. This further minimizes the likelihood of kinking due to the clamp bending against the luer adapter.

In one embodiment, the present invention is implemented as a vascular access device that includes: a catheter adapter comprising a main body portion from which a catheter extends distally and an extension that extends outwardly from the main body portion; extension tubing having a distal end that inserts into and is secured within the extension; and an interface formed of a flexible material that is positioned in-line with the extension such that the extension tubing extends through the interface and into the extension.

In another embodiment, the present invention is implemented as a vascular access device that includes: a catheter adapter; an adapter; extension tubing having a distal end coupled to the catheter adapter and a proximal end coupled to the adapter; and a flexible spacer having a proximal portion that is coupled to a distal end of the adapter and a distal portion that is positioned around the extension tubing.

In another embodiment, the present invention is implemented as a vascular access device that includes: a catheter adapter comprising a main body portion from which a catheter extends distally and an extension that extends outwardly from the main body portion; extension tubing having a distal end that inserts into and is secured within the extension; an adapter coupled to a proximal end of the extension tubing; and a first strain relief feature formed at a catheter adapter end of the extension tubing and a second strain relief feature formed at an adapter end of the extension tubing. The first and second strain relief feature are one of: an interface formed of a flexible material that is positioned in-line with the extension or a distal end of the adapter such that the extension tubing extends through the interface and into the extension or distal end of the adapter; or a flexible spacer having a first end that is coupled to the extension or distal end of the adapter and a second end that is positioned around the extension tubing.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

DETAILED DESCRIPTION OF THE INVENTION

Figure 2:
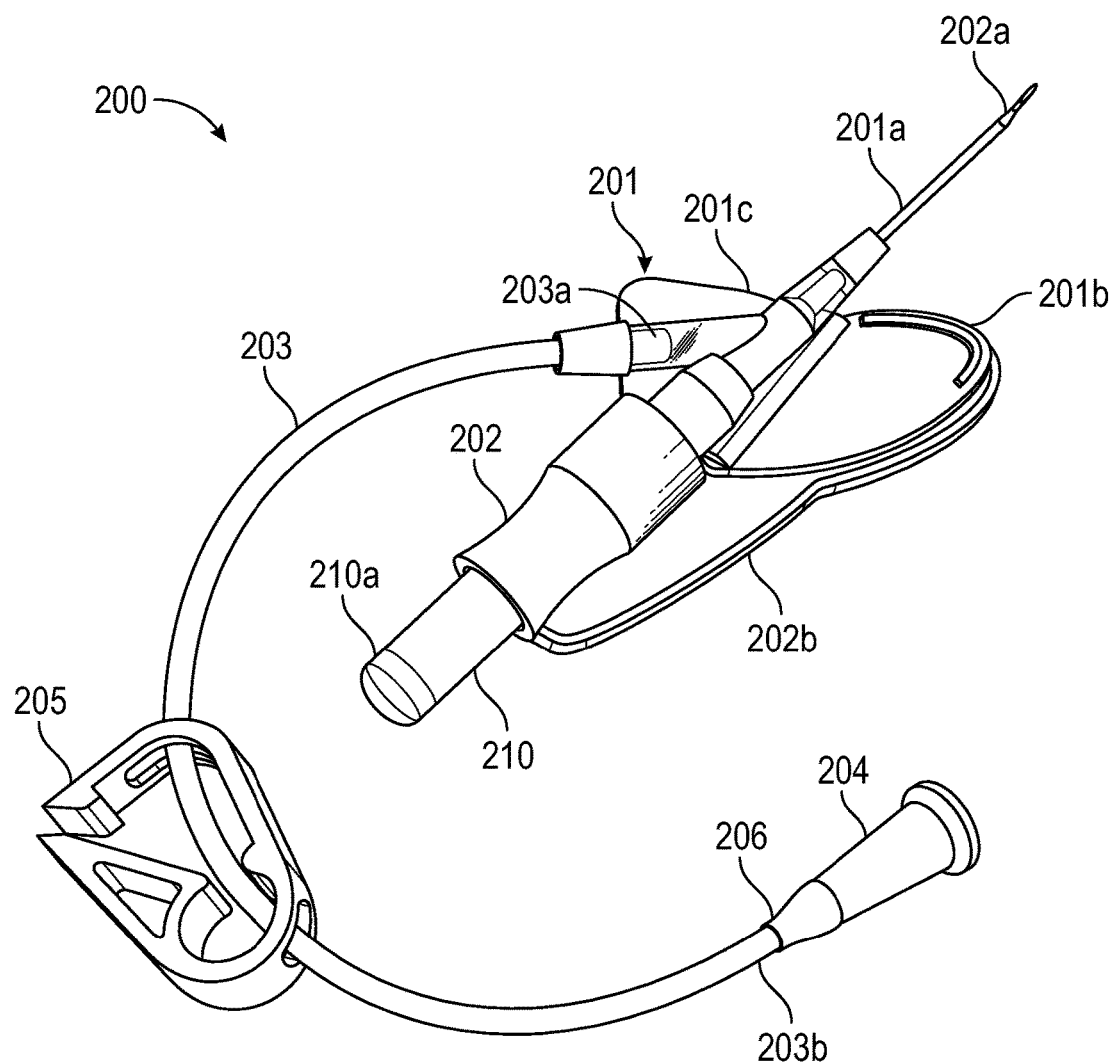
FIG. 2 illustrates a vascular access device configured in accordance with one or more embodiments of the present invention.

FIG. 2 illustrates an example of a vascular access device 200 that is configured in accordance with one or more embodiments of the present invention. Access device 200 includes a catheter adapter 201 from which a catheter 201a extends distally, a needle hub 202 from which a needle 202a extends distally, extension tubing 203 having a distal end 203a that is coupled to catheter adapter 201 and a proximal end 203b coupled to an adapter 204, and a clamp 205 for restricting the flow of fluid through extension tubing 203. Adapter 204 can typically be a luer adapter which is configured to allow other access devices to be coupled to access device 200.

Catheter adapter 201 can include a stabilization platform formed by sides 201b and 201c which extend outwardly from opposite sides of catheter adapter 201. As shown in FIG. 2, in some embodiments access device 200 is configured for right-hand use in that extension tubing 203 couples to the left side of catheter adapter 201 such that stabilization platform side 201b is fully exposed. This can facilitate gripping stabilization platform side 201b with the thumb of the right hand. Of course, in an access device designed for left-hand use, stabilization platform sides 201b, 201c and extension tubing 203 would be on opposite sides of catheter adapter 201 from what is shown in FIG. 2.

Needle hub 202 includes a paddle grip 202b that extends outwardly from the right side of needle hub 202 and has a shape that generally corresponds to the shape of stabilization platform side 201b. Accordingly, paddle grip 202b can be positioned directly beneath stabilization platform side 201b so that stabilization platform side 201b and paddle grip 202b can be sandwiched between the clinician's thumb and index finger during insertion of catheter 201a. By configuring paddle grip 202b in this manner, the clinician can easily withdraw needle hub 202 from catheter adapter 201 by simply sliding the index finger backwards with respect to the thumb thereby causing the paddle grip 202b to slide backward away from stabilization platform side 201b.

Needle hub 202 also includes a flash chamber 210 that is coupled to the proximal end of needle hub 202. Flash chamber 210 can include a plug 210a that allows air to escape through a proximal opening in needle hub 202 while preventing blood from escaping. Also, a proximal end of needle 202a can extend into flash chamber 210 and can include an opening to allow blood to flow out of needle 202a and into flash chamber 210.

Figure 3:
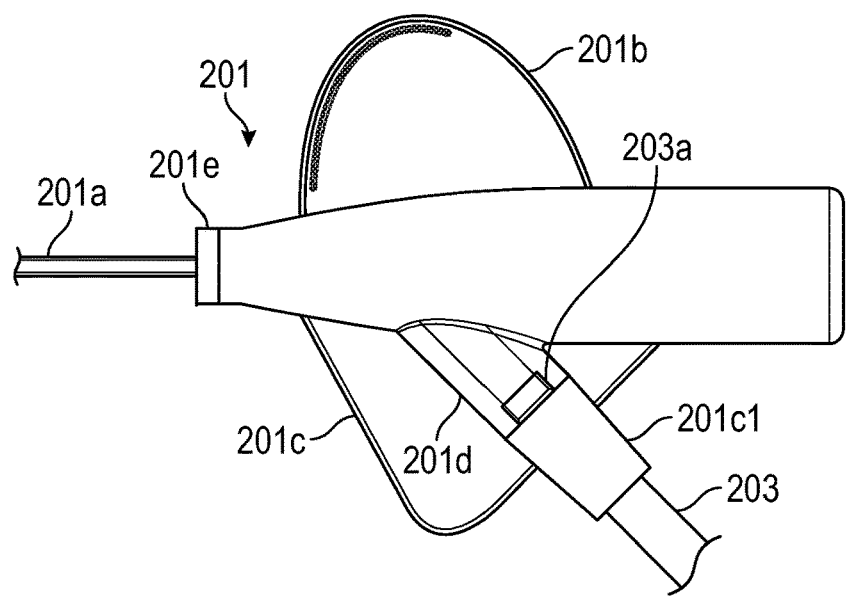
FIG. 3 illustrates a catheter adapter of the vascular access device shown in FIG. 2.
Figure 4:
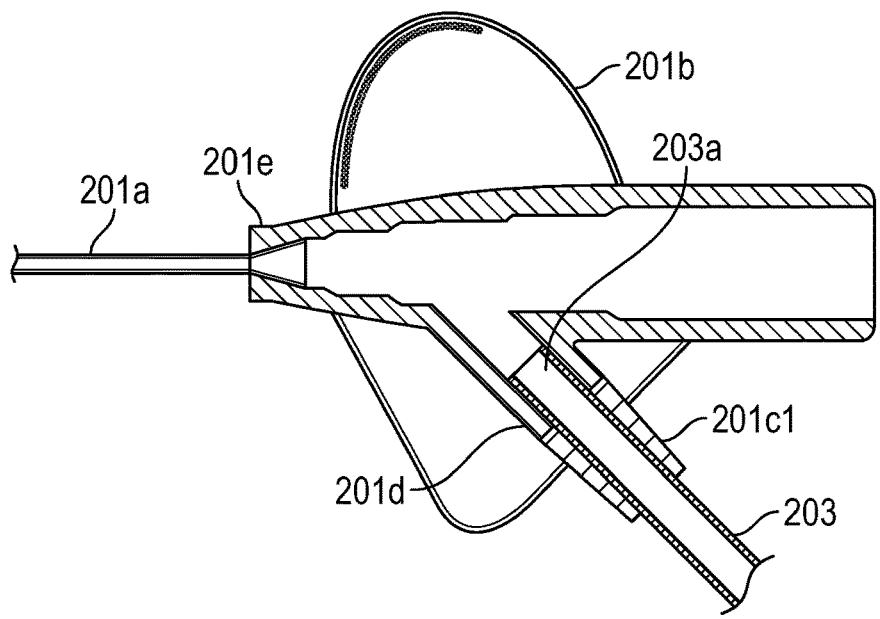
FIG. 4 provides a cross-sectional view of the catheter adapter shown in FIG. 3.

In accordance with embodiments of the present invention and as shown in FIGS. 3 and 4, a main body portion 201e of catheter adapter 201 can include an extension 201d that is integrated into stabilization platform side 201c. Extension 201d can be configured to receive and secure a distal end 203a of extension tubing 203. Both main body portion 201e and extension 201d can be molded from the same material.

Figure 1:
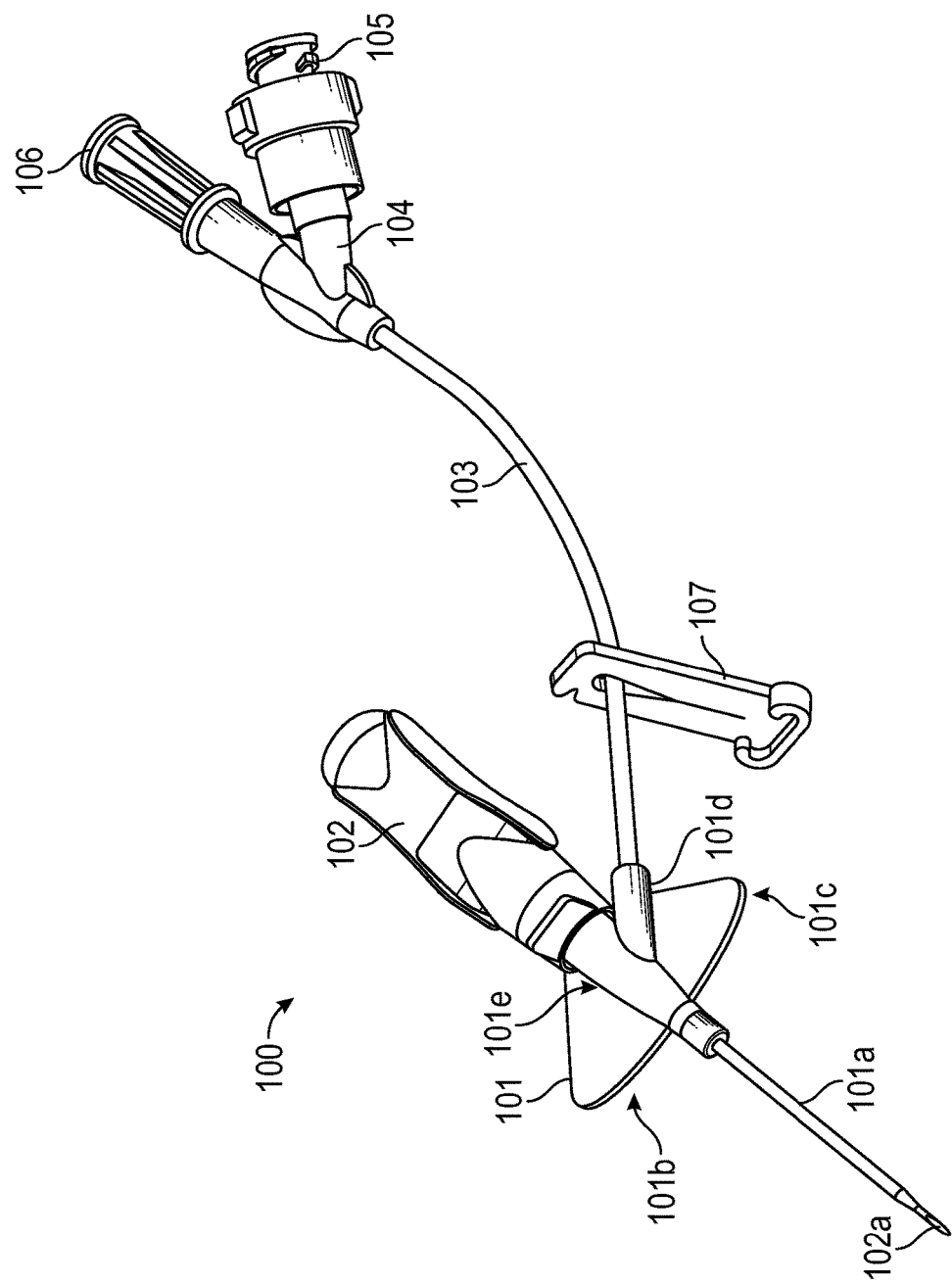
FIG. 1 illustrates a prior art IV access device.

Stabilization platform side 201c can be formed around (e.g., molded around) extension 201d in a manner that produces an interface 201c1 around extension tubing 203. Interface 201c1 can be (but is not required to be) formed of the same material as stabilization platform side 201c which is more flexible than the material used to form main body portion 201e and extension 201d. Once formed, interface 201c1 can function as an end portion of extension 201d. In other words, the combination of extension 201d and interface 201c1 can form a continuous structure through which distal end 203a of extension tubing 203 extends. One of skill in the art will appreciate that interface 201c1 may be incorporated into any stabilization platform of any compatible catheter adapter comprising an integrated extension tube and respective extension. For example, in one embodiment interface 201c1 may be incorporated into or onto extension 101d of prior art device 100 of FIG. 1.

Because interface 201c1 is formed of a more flexible material than extension 201d, kinking is less likely to occur at the interface between extension tubing 203 and extension 201d. In particular, extension tubing 203 can be formed of a material that is substantially flexible to allow adapter 204 to be positioned at any suitable location with respect to catheter adapter 201. Interface 201c1 (as well as stabilization platform side 201c) can be less flexible than extension tubing 203 but more flexible than extension 201d so that the portion of extension tubing 203 within interface 201c1 can bend to some degree, but not enough to form a kink. This transition in flexibility substantially reduces the likelihood that extension tubing 203 will kink.

FIG. 4 provides a cross-sectional view of catheter adapter 201. In this figure, the cross-section is taken along a plane that is just above the top surface of stabilization platform sides 201b and 201c and that extends through main body portion 201e and extension 201d. As shown, main body portion 201e and extension 201d can be molded as a single component. Stabilization platform side 201b, stabilization platform side 201c, and interface 201c1 may also be molded as a single component around catheter adapter 201. Alternatively, stabilization platform side 201c and interface 201c1 could be molded as a single component that is separate from stabilization platform side 201b. In either case, interface 201c1 is an integral portion of stabilization platform side 201c that forms a sleeve-like structure through which extension tubing 203c extends. FIG. 4 also shows that the distal end 203a of extension tubing 203 inserts into extension 201d so that it is secured to catheter adapter 201. Extension 201d and interface 201c1 can therefore form a continuous lumen through which extension tubing 203 inserts.

In other embodiments, interface 201c1 may be formed independently of a stabilization platform. For example, interface 201c1 could be molded around or against extension 201d independently of (e.g., above) stabilization platform side 201b. Alternatively, interface 201c1 could be molded around or against extension 201d on catheter adapters that do not include a stabilization platform or that include only a stabilization platform side on an opposite side of the catheter adapter (e.g., only stabilization platform side 201b).

It is noted that needle hub 202 is not shown in FIGS. 3 and 4. Also, catheter adapter 201 may typically include a septum (not shown) positioned proximal to extension 201d to prevent blood or fluid from flowing proximally out through the proximal opening of catheter adapter 201. Extension 201d is shown as not extending up to or beyond an edge of stabilization platform side 201c. However, in some embodiments, extension 201d may extend farther than what is shown in FIGS. 3 and 4. For example, extension 201d could extend up to and even beyond the edge of stabilization platform side 201c. In such cases, interface 201c1 could be configured to encapsulate a portion of extension 201d as well as to extend beyond an edge of extension 201d in the manner shown in FIGS. 3 and 4.

Figure 5:
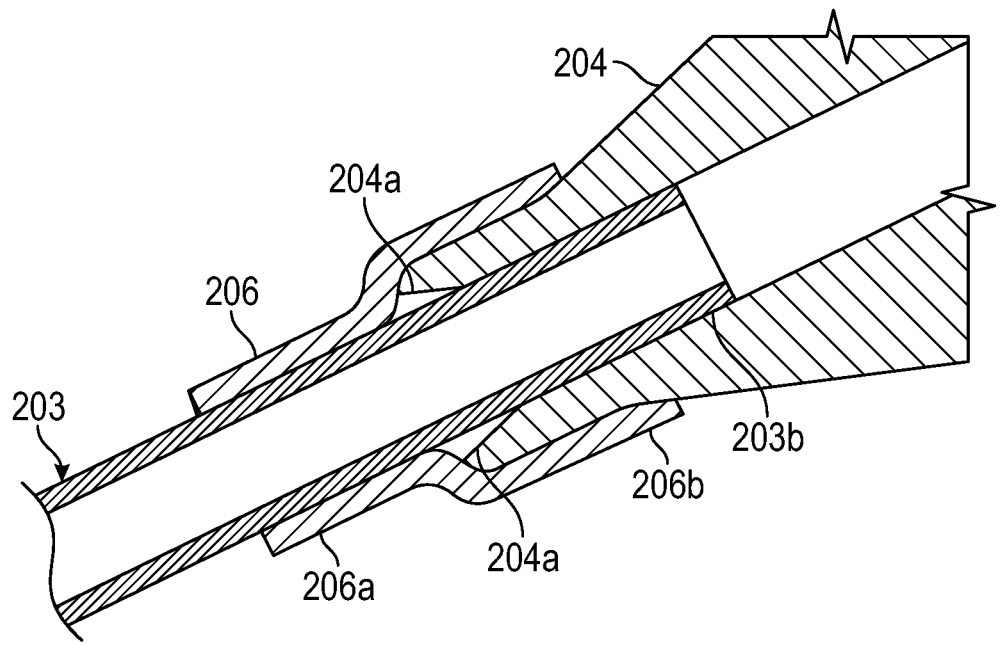
FIG. 5 provides a cross-sectional view of one embodiment of the luer adapter of the vascular access device shown in FIG. 2.
Figure 6:
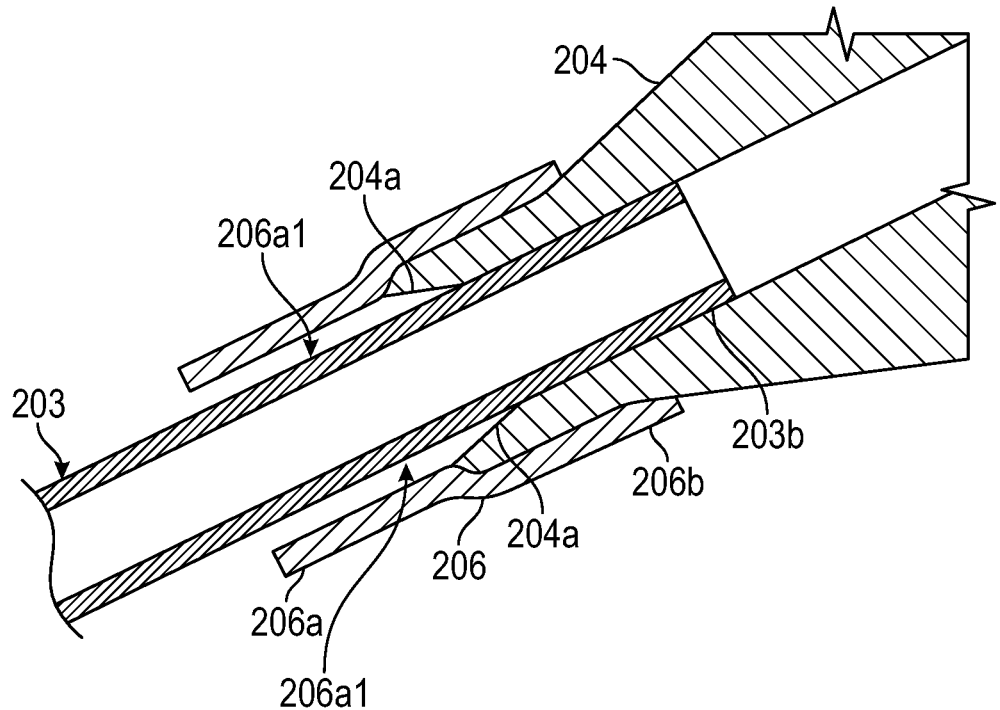
FIG. 6 provides a cross-sectional view of another embodiment of the luer adapter of the vascular access device shown in FIG. 2.

FIGS. 5 and 6 illustrate cross-sectional views of embodiments of a luer adapter 204 that includes a flexible spacer 206. As shown, a proximal end 203b of extension tubing 203 extends into and is secured within luer adapter 204. Flexible spacer 206 has a sleeve shape with an inner diameter that is sufficient to allow flexible spacer 206 to be placed around extension tubing 203. Flexible spacer 206 can also be sufficiently elastic to allow a proximal portion 206b to be placed around a distal end of luer adapter 204. With proximal portion 206b placed around luer adapter 204, flexible spacer 206 will be secured to luer adapter 204 with a distal portion 206a being positioned around extension tubing 203. Distal portion 206a can provide reinforcement at the interface between luer adapter 204 and extension tubing 203 thereby minimizing the likelihood that extension tubing 203 will become kinked at the interface.

In some embodiments, such as is shown in FIGS. 5 and 6, the distal opening of luer adapter 204 can include a chamfered surface 204a. Chamfered surface 204a allows extension tubing 203 to bend slightly prior to contacting the distal edge of luer adapter 204. As shown in FIG. 6, in some embodiments, the inner diameter of flexible spacer 206 can be greater than the outer diameter of extension tubing 203 and substantially equal to the diameter at the distalmost point of chamfered surface 204a. In such cases, a space 206a1 will exist between extension tubing 203 and distal portion 206a.

Flexible spacer 206 can be a separate component from extension tubing 203 and luer adapter 204. As a separate component, flexible spacer 206 can be formed of a suitable elastic material that is different than the material used to form luer adapter 204. In some embodiments, flexible spacer 206 can have an outer diameter that is greater than an inner diameter of the channel or opening in clamp 205 through which extension tubing 203 extends. In this way, flexible spacer 206 can function to prevent clamp 205 from being positioned too close to luer adapter 204. In particular, if clamp 205 clamps extension tubing 203 at the interface between extension tubing 203 and luer adapter 206, it would cause extension tubing 203 to be more likely to kink at the interface when it is bent against the distal end of the luer adapter 204. Flexible spacer 206 can also be employed to ensure that clamp 205 cannot clamp extension tubing 203 near the interface.

Although the above description describes forming interface 201c1 only at the catheter adapter end of the extension tubing and describes incorporating flexible spacer 206 only at the luer adapter end of the extension tubing, these techniques could be applied on the opposite ends of the extension tubing. For example, an interface similar to interface 201c1 could be formed on a distal end of luer adapter 204 around extension tubing 203 in place of flexible spacer 206. This could be accomplished by separately molding an interface from a flexible material around the distal end of luer adapter 204 (e.g., with reference to the figures, extension 201d could be viewed as the distal end of luer adapter 204). Alternatively, in embodiments where luer adapter 204 includes a component that is molded of a flexible material, the interface could be integrally formed within the component in a similar manner as interface 201c1 can be integrally formed within stabilization platform side 201c. For example, if luer adapter 204 includes a soft grip feature, this soft grip feature could be extended to form an interface at the distal end of luer adapter 204.

Similarly, a flexible spacer could be employed at the catheter adapter end of the extension tubing in place of interface 201c1. This could be accomplished by placing a distal portion of a flexible spacer around (or otherwise secured to) extension 201d. In such cases, extension 201d could be configured with a chamfer similar to what is shown in FIGS. 5 and 6. As described above, a flexible spacer could be employed in this manner in any configuration of a catheter adapter that includes extension 201d including those with or without a stabilization platform.

Various embodiments of the present invention further comprise a safety mechanism configured to secure the sharpened, distal tip of the introducer needle following removal and separation of the needle hub from the catheter adapter. A safety mechanism may include any compatible device known in the art. In some instances, the safety mechanism is configured to interact with a needle feature, such as a ferrule, notch, crimp or bump on the cannula. The crimp or bump formed in the cannula causes a slight out of round configuration that can be used to activate a safety mechanism. In some instance, the safety mechanism comprises an arm or lever that is actuated to capture the needle tip within the mechanism and prevent the tip from emerging prior to safe disposal.

The safety mechanism is attached to the body of the needle and is capable of sliding along the length thereof. In some instances, an initial or assembled position of the safety mechanism is located in proximity to the base or proximal end of the catheter adapter prior to catheterization. For some configurations, the assembled position of the safety mechanism is between the proximal end of the needle hub and the proximal end of the catheter adapter or stabilization platform, wherein the safety mechanism does not overlap the catheter adapter or stabilization platform. In some instances, a portion of the safety mechanism is positioned within the catheter adapter, with the balance of the safety mechanism being positioned external to the catheter adapter, such as within the needle hub. In some embodiments, a portion of the catheter adapter or stabilization platform is extended proximally to provide a housing in which at least a portion of the safety mechanism is housed. In some instances, the entire safety mechanism is housed within the housing of the catheter adapter or stabilization platform prior to catheterization.

In some embodiments, the assembled position of the safety mechanism positions the proximal end of the catheter adapter between the distal end of the safety mechanism and a distal end of a paddle grip of the needle hub. In some instances, the assembled position of the safety mechanism positions the proximal end of the catheter adapter between the distal end of the safety mechanism and a proximal end of a paddle grip of the needle hub. In some instances, a portion of the safety mechanism overlaps a portion of a paddle grip of the needle hub. In some embodiments, at least some portion of at least one of the catheter adapter and the paddle grip overlaps at least some portion of the safety mechanism. In some embodiments, no portion of the catheter adapter or paddle grip overlaps any portion of the safety mechanism.

In some embodiments, a defeatable mechanical connection is provided between the safety mechanism and at least one other component of the access device. In some embodiments, a distal end of the safety mechanism is selectively coupled to a proximal end of the catheter adapter. In one embodiment, the safety mechanism interlocks internally to the proximal end of the catheter adapter. In one embodiment, the safety mechanism interlocks externally to the proximal end of the catheter adapter. In some embodiments, a distal end of the safety mechanism is selectively coupled to a proximal end of the stabilization platform. In some embodiments, a surface of the safety mechanism is selectively coupled to at least one surface of at least one of the catheter adapter, a blood control valve, an extension tube, and the stabilization platform. In some instances, the mechanical connection is defeated upon securement of the needle tip within the safety mechanism.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A vascular access device comprising:
   a catheter adapter comprising a main body portion, an extension, and a catheter, wherein the main body portion comprises a proximal end and a distal end aligned with the proximal end, wherein the catheter extends distally from the distal end, wherein the extension extends outwardly from the main body portion and is disposed between the proximal end and the distal end, wherein the extension is constructed of a first material;
   a stabilization platform extending outwardly from the catheter adapter, wherein the stabilization platform comprises a wing;
   extension tubing having a distal end that inserts into and is secured within the extension; and
   an interface coupled to a proximal-most surface of the extension and formed of a second material, wherein the second material is more flexible than the first material, wherein the extension tubing extends through and proximally from the interface, wherein the interface is an integral portion of the stabilization platform.

2. The vascular access device of claim 1, further comprising:
   a stabilization platform having a first stabilization platform side that is coupled to the catheter adapter and extends outwardly from the main body portion.

3. The vascular access device of claim 2, wherein the interface is an integral part of the first stabilization platform side.

4. The vascular access device of claim 2, wherein the first stabilization platform side is molded around a portion of the extension.

5. The vascular access device of claim 1, wherein the interface:
   extends around a portion of the extension; or
   is molded to the extension.

6. The vascular access device of claim 2, wherein the first stabilization platform side and the extension are formed of the same flexible material.

7. The vascular access device of claim 1, wherein the first stabilization platform side extends outwardly from the main body portion farther than the extension.

8. The vascular access device of claim 1, further comprising:
   an adapter coupled to a proximal end of the extension tubing; and
   a flexible spacer having a proximal portion that is coupled to a distal end of the adapter and a distal portion that is positioned around the extension tubing.

9. The vascular access device of claim 8, wherein the flexible spacer is a separate component from the adapter.

10. The vascular access device of claim 8, wherein a distal opening of the adapter includes a chamfered surface.

11. The vascular access device of claim 10, wherein an inner diameter of the flexible spacer is substantially equal to a diameter at the distalmost portion of the chamfered surface.

12. The vascular access device of claim 8, further comprising:
   a clamp having an opening through which the extension tubing extends to secure the clamp to the extension tubing, the opening having a diameter, and wherein an outer diameter of the flexible spacer is greater than the diameter of the opening to prevent the clamp from extending overtop the flexible spacer.

13. A vascular access device comprising:
   a catheter adapter;
   a luer adapter, comprising a chamfered surface;
   extension tubing having a distal end coupled to the catheter adapter and a proximal end coupled to the luer adapter; and
   a flexible spacer having a proximal portion that couples to a distal end of the luer adapter and a distal portion that is positioned around the extension tubing, wherein the luer adapter is disposed between the proximal portion of the flexible spacer and the extension tubing, wherein the distal portion of the flexible spacer is spaced apart from the extension tubing to form a space, wherein the chamfered surface of the luer adapter is proximate the space.

14. The vascular access device of claim 13, wherein a distal opening of the luer adapter includes the chamfered surface.

15. The vascular access device of claim 14, wherein an inner diameter of the proximal portion of the flexible spacer is substantially equal to an outer diameter of the luer adapter.

16. The vascular access device of claim 13, wherein the catheter adapter comprises a main body portion from which a catheter extends and an extension that extends outwardly from the main body portion, the distal end of the extension tubing inserting into the extension, the vascular access device further comprising:
   an interface formed of a flexible material that is positioned in-line with the extension such that the extension tubing extends through the interface and into the extension.

17. The vascular access device of claim 16, wherein the interface has a sleeve shape that encircles the extension tube.

18. The vascular access device of claim 16, further comprising:
   a stabilization platform having a first stabilization platform side that is coupled to the catheter adapter and extends outwardly from the main body portion, wherein the interface is one of:
   an integral part of the first stabilization platform side; or
   a separate part from the first stabilization platform side.

19. The vascular access device of claim 18, wherein the interface extends beyond an edge of the first stabilization platform side.

20. A vascular access device comprising:
   a catheter adapter comprising a main body portion, an extension, and a catheter, wherein the main body portion comprises a proximal end and a distal end aligned with the proximal end, wherein the catheter extends distally from the distal end, wherein the extension extends outwardly from the main body portion and is disposed between the proximal end and the distal end, wherein the extension is constructed of a first material;
   extension tubing having a distal end that inserts into and is secured within the extension;
   a luer adapter coupled to a proximal end of the extension tubing, wherein the luer adapter comprises a chamfered surface;
   a flexible spacer having a proximal portion, a distal portion, and a transition portion disposed between the proximal portion and the distal portion, wherein the proximal portion is coupled to a distal end of the luer adapter and the distal portion is positioned around the extension tubing, wherein the luer adapter is disposed between the proximal portion of the flexible spacer and the extension tubing, wherein the proximal portion comprises a first inner diameter, wherein the distal portion comprises a second inner diameter, wherein the first inner diameter is greater than the second inner diameter, wherein the second inner diameter of the distal portion of the flexible spacer is substantially equal to an outer diameter of the extension tubing; and
   a space enclosed by the chamfered surface, the extension tubing, and the transition portion.

\* \* \* \* \*